US012558390B2

(12) United States Patent
Wu

(10) Patent No.: US 12,558,390 B2
(45) Date of Patent: Feb. 24, 2026

(54) SUPPLEMENT COMPOSITIONS

(71) Applicant: Ming Jie Wu, Maynard, MA (US)

(72) Inventor: Ming Jie Wu, Maynard, MA (US)

( * ) Notice: Subject to any disclaimer, the term of this patent is extended or adjusted under 35 U.S.C. 154(b) by 526 days.

(21) Appl. No.: 17/990,699

(22) Filed: Nov. 20, 2022

(65) Prior Publication Data

US 2023/0158092 A1 May 25, 2023

Related U.S. Application Data

(60) Provisional application No. 63/281,465, filed on Nov. 19, 2021.

(51) Int. Cl.

| | |
|---|---|
| *A61K 36/428* | (2006.01) |
| *A23L 33/105* | (2016.01) |
| *A61K 35/586* | (2015.01) |
| *A61K 36/062* | (2006.01) |
| *A61K 36/074* | (2006.01) |
| *A61K 36/233* | (2006.01) |
| *A61K 36/258* | (2006.01) |
| *A61K 36/288* | (2006.01) |
| *A61K 36/537* | (2006.01) |
| *A61K 36/539* | (2006.01) |
| *A61K 36/75* | (2006.01) |
| *A61K 36/758* | (2006.01) |
| *A61K 36/79* | (2006.01) |
| *A61K 36/90* | (2006.01) |
| *A61K 36/9066* | (2006.01) |

(52) U.S. Cl.
CPC .......... *A61K 36/428* (2013.01); *A23L 33/105* (2016.08); *A61K 35/586* (2013.01); *A61K 36/062* (2013.01); *A61K 36/074* (2013.01); *A61K 36/233* (2013.01); *A61K 36/258* (2013.01); *A61K 36/288* (2013.01); *A61K 36/537* (2013.01); *A61K 36/539* (2013.01); *A61K 36/75* (2013.01); *A61K 36/758* (2013.01); *A61K 36/79* (2013.01); *A61K 36/90* (2013.01); *A61K 36/9066* (2013.01)

(58) Field of Classification Search
None
See application file for complete search history.

(56) References Cited

U.S. PATENT DOCUMENTS

| | | | |
|---|---|---|---|
| 5,494,668 | A | 2/1996 | Patwardhan |
| 5,565,199 | A | 10/1996 | Page et al. |
| 5,707,630 | A | 1/1998 | Morrow |
| 5,854,291 | A | 12/1998 | Laughlin et al. |
| 5,910,307 | A | 6/1999 | Kwak et al. |
| 5,916,565 | A | 6/1999 | Rose et al. |
| 5,985,282 | A | 11/1999 | Haveson |
| 6,060,063 | A | 5/2000 | Lansky |
| 6,200,594 | B1 | 3/2001 | Ernest et al. |
| 2007/0020346 | A1 | 1/2007 | Xing et al. |
| 2007/0026109 | A1 | 2/2007 | Foulger |
| 2016/0243180 | A1 | 8/2016 | Ko et al. |
| 2017/0128514 | A1 | 5/2017 | Du et al. |

FOREIGN PATENT DOCUMENTS

WO      WO-0122934 A2 *   4/2001   .............. A61P 43/00

OTHER PUBLICATIONS

Yang, F. et al., "Radix Bupleuri: A Review of of Traditional Uses, Botany, Phytochemistry, Pharmacology, . . . " BioMed Research International, 2017: 7597596, 1-22 (2017).
Liang, G. et al., "Protective effects of Rhizoma smilacis glabrae extracts on potassium oxonate- and monosodium urate-induced . . . " Phytomedicine, (Jun. 2019) 59:152772.
Lu, Y. et al., "Analysis of Schisandra chinensis and Schisandra sphenanthera". J of Chromatography A. 1216 (11): 1980-90 (Mar. 2009).

* cited by examiner

*Primary Examiner* — Susan Hoffman
(74) *Attorney, Agent, or Firm* — Milstein Zhang & Wu LLC; Duan Wu, Esq.

(57) ABSTRACT

The invention provides unique compositions containing mixtures of extracts from medicinal plants and animal parts, as well as related uses for improving health and treating diseases. The inventive compositions provide a wide range of health benefits in the human body in comparison to effects from individual components contained therein.

19 Claims, No Drawings

SUPPLEMENT COMPOSITIONS

CROSS-REFERENCE TO RELATED APPLICATIONS

This application claims priority to and the benefit of co-pending U.S. provisional patent applications Ser. No. 63/281,465, filed Nov. 19, 2021, which application is incorporated herein by reference in its entirety.

FIELD OF THE INVENTION

The invention relates to dietary or nutritional supplements, specifically herbal supplements that include extracts from traditional Chinese medicinal plants or fungi, as well as methods of their use for purpose of improving the health and wellness of a patient including alleviating or preventing symptoms from certain diseases and conditions including cancer.

BACKGROUND OF THE INVENTION

Natural botanical products including traditional medicinal plants, animals and their parts and extracts have long been used in many parts of the world such as China and its surrounding countries for health benefits. These benefits include improvements in an individual person's general wellness and health, as well as in terms of treating, therapeutically or prophylactically, symptoms associated with certain diseases and conditions. However, it can be tricky to find the right combination of extracts from these medicinal plants or herbs in order to avoid significant side effects while accentuating or retaining their potency especially when these extracts are blended directly with each other or with minimal processing. As is well known to practitioners of traditional herbal medicine, different plants can be natural antidotes to neutralize each other, while others can enhance a desired medicinal effect or offer synergetic benefits and advantages.

Ingredients or extracts from plants have been used as dietary supplements or pharmaceutical products as treatment or prophylactic to various symptoms, conditions and diseases in human, including preparations against cancer, inflammation, joint and muscle pain, cardiovascular diseases, hormonal imbalance and so on. Examples of such use can be found in U.S. Pat. Nos. 5,494,668, 5,916,565, 5,707, 630, 5,565,199, 5,910,307, 6,200,594, or Application Nos. 20070020346, 20160243180, and 20170128514. Treatment using supplements from natural herbs or plants are generally of low toxicity or side effects. This has been at least partly attributed to our body's natural ability to selectively absorb beneficial ingredients from a diet sourced from nature.

By contrast, conventional pharmaceutical preparations often come with strong side effects. For instance, chemotherapy, routinely used to treat cancer, often causes nausea, vomiting, fatigue, stomatitis, esophagitis, or diarrhea in patients being treated. Thus, there is a continuing need to develop largely botanical anticancer and other disease-fighting formulations, whether as supplements or pharmaceuticals.

SUMMARY OF THE INVENTION

In one aspect, the invention relates to combinatory compositions or mixtures of extracts from multiple medicinal plants, fungi, herbs and/or animal parts. In various embodiments, any four, five, six, seven, eight, nine, ten, eleven, twelve, thirteen, or fourteen items (preferably ten or more) from the following list of medicinal plant/fungi/animal extracts can be selected and mixed to make the inventive composition: Tu Gua Gen (Radix *Trichosanthes cucumeroides*), Rue (*Ruta graveolens*), Liang Mian Zhen (*Zanthoxylum nitidum*), Dong Chong Xia Cao (*Ophiocordyceps sinensis*), Pu Gong Ying (*Taraxacum*), Ban Zhi Lian (*Scutellaria barbata*), Dan Shen (*Salvia miltiorrhiza*), Jiang Huang (*Curcuma longa*), Tu Fu Ling (*Smilacis Glabrae*), Wu Wei Zi (*Schisandra chinensis*), Chai Hu (Radix *Bupleuri*), Ling Zhi (*Ganoderma lucidum*), Ren Shen/Ginseng (*Panax*), and Bie Jia (*Carapax Trionycis*).

In one feature, the inventive composition preferably includes an extract from Tu Gua Gen (Radix *Trichosanthes cucumeroides*), more preferably, at about 20% of the composition by weight. In various embodiments, the inventive composition further includes extracts from Dan Shen (*Salvia miltiorrhiza*), Tu Fu Ling (*Smilacis Glabrae*), and Bie Jia (*Carapax Trionycis*), preferably each at a ratio of 1:2 compared to Tu Gua Gen (Radix *Trichosanthes cucumeroides*), i.e., each at about 10% of the composition by weight. The inventive composition may further include extracts from any number of the remaining ten components from the list in the immediately preceding paragraph, preferably each at a ratio of 1:4 compared to Tu Gua Gen (Radix *Trichosanthes cucumeroides*), i.e., each at about 5% of the composition by weight. In a preferred embodiment, the composition of the invention includes at least extracts from each of the following: Tu Gua Gen (Radix *Trichosanthes cucumeroides*), Dan Shen (*Salvia miltiorrhiza*), Dong Chong Xia Cao (*Ophiocordyceps sinensis*), and Ling Zhi (*Ganoderma lucidum*).

In a particularly preferred embodiment, the present invention provides a combination composition as follows:

1) a Tu Gua Gen (Radix *Trichosanthes cucumeroides*) extract about 20%, i.e., 18%-22%, by weight;
2) a Rue (*Ruta graveolens*) extract about 5%, i.e., 4.5%-5.5%, by weight;
3) a Liang Mian Zhen (*Zanthoxylum nitidum*) extract about 5%, i.e., 4.5%-5.5%, by weight;
4) a Dong Chong Xia Cao (*Ophiocordyceps sinensis*) extract about 5%, i.e., 4.5%-5.5%, by weight;
5) a Pu Gong Ying (*Taraxacum*) extract about 5%, i.e., 4.5%-5.5%, by weight;
6) a Ban Zhi Lian (*Scutellaria barbata*) extract about 5%, i.e., 4.5%-5.5%, by weight;
7) a Dan Shen (*Salvia miltiorrhiza*) extract about 10%, i.e., 9%-11%, by weight;
8) a Jiang Huang (*Curcuma longa*) extract about 5%, i.e., 4.5%-5.5%, by weight;
9) a Tu Fu Ling (*Smilacis Glabrae*) extract about 10%, i.e., 9%-11%, by weight;
10) a Wu Wei Zi (*Schisandra chinensis*) extract about 5%, i.e., 4.5%-5.5%, by weight;
11) a Chai Hu (Radix *Bupleuri*) extract about 5%, i.e., 4.5%-5.5%, by weight;
12) a Ling Zhi (*Ganoderma lucidum*) extract about 5%, i.e., 4.5%-5.5%, by weight;
13) a Ren Shen/Ginseng (*Panax*) extract about 5%, i.e., 4.5%-5.5%, by weight; and
14) a Bie Jia (*Carapax Trionycis*) extract about 10%, i.e., 9%-11%, by weight.

In an embodiment, the present invention provides a formula that can be made into a supplement to a person's diet. In an alternate embodiment, the present invention provides a pharmaceutical composition, which includes the formula described herein and may further include a pharmaceutically acceptable carrier, additive or excipient. The inventive composition can be made into any conventional forms for oral administration including as a tablet or as a capsule where the extract ingredients are in solid (e.g., powder), semiliquid (e.g., gel) or liquid form.

In a feature, the composition or formula disclosed herein provides health benefits by energizing the "qi" and meridian, or otherwise increasing lymphatic circulation in the body. This helps to both strengthen the functionality of a person's immune system and assist in the metabolic process, which, in an embodiment, can be used to support a patient's immune and metabolic functions especially for those suffering from diseases such as cancer or having undergone medical treatment such as chemotherapy. In various embodiments, the kinds of cancer being treated include lymphoma, leukemia, nasopharyngeal carcinoma, liver cancer, colorectal cancer, esophageal cancer, thoracic cancer, and so on.

In another aspect, the invention features a method of strengthening a person's immune system and/or improving one's metabolism, where the method includes a step of administering to the person the composition of the invention. In an embodiment, the method is used to treat cancer in the person.

In an embodiment, the invention provides a method of treating a disease, e.g., cancer, in a person, where the method includes the step of administering to the person a composition that includes pharmaceutically effective amounts of each of the following extracts: Tu Gua Gen (Radix *Trichosanthes cucumeroides*), Dan Shen (*Salvia miltiorrhiza*), Dong Chong Xia Cao (*Ophiocordyceps sinensis*), and Ling Zhi (*Ganoderma lucidum*). In various embodiments, the composition administered further includes pharmaceutically effective amounts of one or more of the other ten medicinal extracts disclosed herein.

In a preferred embodiment, the invention provides a method of treating a disease, e.g., cancer, in a person, where the method includes a step of administering to the person a composition that includes:

(1) the Tu Gua Gen (Radix *Trichosanthes cucumeroides*) extract about 20% by weight;

(2) the Rue (*Ruta graveolens*) extract about 5% by weight;

(3) the Liang Mian Zhen (*Zanthoxylum nitidum*) extract about 5% by weight;

(4) the Dong Chong Xia Cao (*Ophiocordyceps sinensis*) extract about 5% by weight;

(5) the Pu Gong Ying (*Taraxacum*) extract about 5% by weight;

(6) the Ban Zhi Lian (*Scutellaria barbata*) extract about 5% by weight;

(7) the Dan Shen (*Salvia miltiorrhiza*) extract about 10% by weight;

(8) the Jiang Huang (*Curcuma longa*) extract about 5% by weight;

(9) the Tu Fu Ling (*Smilacis Glabrae*) extract about 10% by weight;

(10) the Wu Wei Zi (*Schisandra chinensis*) extract about 5% by weight;

(11) the Chai Hu (Radix *Bupleuri*) extract about 5% by weight;

(12) the Ling Zhi (*Ganoderma lucidum*) extract about 5% by weight;

(13) the Ren Shen/Ginseng (*Panax*) extract about 5% by weight; and

(14) the Bie Jia (*Carapax Trionycis*) extract about 10% by weight.

The foregoing and other objects, aspects, features, and advantages of the invention will become more apparent from the following description and from the claims.

DETAILED DESCRIPTION OF THE INVENTION

I. Definition

Unless otherwise noted, technical terms are used according to conventional usage.

As used in the specification and claims, the singular form "a", "an", or "the" includes plural references unless the context clearly dictates otherwise. For example, the term "a cell" includes a plurality of cells including mixtures thereof. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent," or "except for [a particular feature or element]," or "wherein [a particular feature or element] is not present (included, etc.) . . . ".

As used herein, "about" means within plus or minus 10%. For example, "about 1" means "0.9 to 1.1", "about 2%" means "1.8% to 2.2%", "about 2% to 3%" means "1.8% to 3.3%", and "about 3% to about 4%" means "2.7% to 4.4%."

As used herein, the term "effective amount" refers to the amount of the substance that will contribute toward the overall composition's ability to provide a desired health benefit.

As used herein, "extract" means a part, portion or substance removed from a plant or animal, especially a concentrated preparation of one or more plant or animal components. One way of preparing an extract is simply removing excess water content from a targeted or harvested part, e.g., through a drying process such as under the sun or in a hot oven. Another way of preparing an extract involves dissolving the part in a solvent, e.g., an alcohol, before separating the target substance from the solution. Other mechanical or chemical processes can be used to procure an extract from a plant or animal part, e.g., pressing, crushing, separating, grinding, sifting, and/or distilling.

As used herein, the term "subject" refers to any animal (e.g., a mammal), including, but not limited to, human/person. Typically, the terms "subject," "person," and "patient" are used interchangeably herein in reference to a human subject.

Terms such as "treating" or "treatment" or "to treat" or "alleviating" or "to alleviate" as used herein refer to both (1) therapeutic measures that cure, slow down, lessen symptoms of, and/or halt progression of a diagnosed pathologic condition or disorder and (2) prophylactic or preventative measures that prevent or slow the development of a targeted pathologic condition or disorder. Thus, those in need of treatment include those already with the disorder; those prone to have the disorder; and those in whom the disorder is to be prevented. For example, a subject is successfully "treated" for cancer according to methods of the present invention if the patient shows one or more of the following: a reduction in the number of or complete absence of cancer cells; a reduction in the tumor size; inhibition of or an absence of cancer cell infiltration into peripheral organs including the spread of cancer into soft tissue and bone; inhibition of or an absence of tumor metastasis; inhibition or an absence of tumor growth; relief of one or more symptoms associated with the specific cancer; reduced morbidity and mortality; and/or improvement in quality of life.

One of the problems that the inventor set out to address in existing supplements is the following: some of the current supplements in the market aim to address the patient's weakened immune system, but none seems to be addressing the patient's compromised metabolism at the same time. In cancer patients, as the disease progresses or treatment intensifies, symptoms or side effects such as nausea, vomiting and anorexia, impact a patient's ability for normal nutritional intake and energy conversion. This leads to wasting and further weakens the immune system.

Accordingly, the present invention aims to provide compositions and formula based largely on herbal remedies to provide support for a patient, e.g., a cancer patient, in terms of boosting or improving both the immune system and the metabolism functionality. As used herein, the terms "strengthening" "supporting" "boosting" "improving" the immune system or similar terms refer to improvement in one or more aspects of a patient's immune functions, e.g., higher quantity and/or quality of disease-and-infection-fighting immunoglobulins, leukocytes, lymphocytes, T cells, Natural Killer (NK) cells, monocytes, and so on, in patient blood.

As used herein, the terms "strengthening" "restoring" "boosting" "improving" the metabolism or similar terms refer to improvement in one or more aspects of a patient's metabolism involving bodily functions related to digestion, breathing, circulation and the function of organs, muscles and nervous system; the improvement confirmed as normalization or improvement in measurable metabolites in the patient's blood such as amounts of glucose, calcium, electrolytes, creatinine, and/or blood urea nitrogen (BUN).

While not wishing to be bound by any particular theory, the inventive formula disclosed herein combines herbs that promote blood and qi circulation and remove stasis, such as Radix *Trichosanthes cucumeroides* and *Salvia miltiorrhiza*, with herbs that help support the immune system, such as *Ophiocordyceps sinensis* and *Ganoderma lucidum*. In addition, other medicinal extracts are preferably added to the combination composition, at particular ratios, to achieve a synergetic effect that optimizes various bodily functions for person under stress, whether coming from a disorder such as cancer or a treatment regimen such as chemotherapy. Therefore, the disclosed compositions and resulting products can help restore and boost patients' metabolic functions as well as their immune system. This ensures that the disclosed products, as a pharmaceutical or dietary supplement, provide more health benefits than other herb-based products on the market, because the presently disclosed product can help stimulate the healing potential within the patients.

The natural sources including fungi, medicinal plants and animal parts used in the present invention include: Tu Gua Gen (Radix *Trichosanthes cucumeroides*), Rue (*Ruta graveolens*), Liang Mian Zhen (*Zanthoxylum nitidum*), Dong Chong Xia Cao (*Ophiocordyceps sinensis*), Pu Gong Ying (*Taraxacum*), Ban Zhi Lian (*Scutellaria barbata*), Dan Shen (*Salvia miltiorrhiza*), Jiang Huang (*Curcuma longa*), Tu Fu Ling (*Smilacis Glabrae*), Wu Wei Zi (*Schisandra chinensis*), Chai Hu (Radix *Bupleuri*), Ling Zhi (*Ganoderma lucidum*), Ren Shen/Ginseng (*Panax*), and Bie Jia (*Carapax Trionycis*).

Tu Gua Gen (Radix *Trichosanthes cucumeroides, Radix Trichosanthes cucumeroides* or, more general, *Trichosanthes cucumeroides*) is also known as the root (radix) of: Wang Gua, Japanese snake gourd, *Trichosanthes Pilosa,* or *Trichosanthes ovigera.* Cultivated in parts of East Asia and Southeast Asia, it contains β-carotin, fatty acids, amino acids, vitamin C, Lycopene and so on. It is used for detoxication, improving circulation, and sometimes as cosmetics or antioxidant. The root of *T. cucumeroides* can be harvested, washed in water, dried, and pressed or ground to powder for medicinal use.

Rue (*Ruta graveolens*) is also known as common rue or herb-of-grace. It is widely used all over the world for medicinal use, including as an antidote to venomous snake bites in ancient Rome. However, rue extract is hepatotoxic and can cause gastric pain, vomiting and skin burn, and therefore, should be used with care. Rue extracts can be prepared by drying the plant and grinding into powder for practicing the present invention.

Liang Mian Zhen (*Zanthoxylum nitidum*) is known to remove stasis, promote the circulation of qi, alleviate pain, and dredge meridians. It is also used for removing toxicity from the body and resolving swelling or inflammation when applied topically. The medicinal parts of *Zanthoxylum nitidum* include its root, stem, and other parts of the plant, and are typically harvested throughout the year, washed in water, sliced or sectioned, dried under the sun and then ground to powder. A preferred medicinal part of *Zanthoxylum nitidum* is its root (Radix *Zanthoxylum nitidum*).

Dong Chong Xia Cao (*Ophiocordyceps sinensis*) is known in English colloquially as caterpillar fungus, or by its more prominent name yartsa gunbu. An entomopathogenic fungus, *Ophiocordyceps sinensis* can be mainly found in the Tibetan Plateau and the Himalayan regions. It parasitizes the larvae of moths in the family Hepialidae and produces a fruiting body that is used in traditional Chinese medicine as an herbal remedy. It contains the compound Cordycepin. The dark-brown stalk-like fruiting body is typically harvested by hand and can be dried, sectioned or processed into powder.

Pu Gong Ying (*Taraxacum*) is commonly known as dandelion, and also as *Taraxacum herba* or *Taraxacum officinale*. The entire plant, including its root, stem, leaves and flower can be used for medicinal use. It is considered to bring about many health benefits, including lowering cholesterol, regulating blood sugar and blood pressure, boosting immunity and aiding digestion. Its parts can be dried, sliced and processed mechanically into powder.

Ban Zhi Lian (*Scutellaria barbata*) is a flowering plant in the mint family, Lamiaceae. Sometimes known as barbed skullcap, the perennial herb has been used to treat cancer, hepatitis, and pulmonary abscess. It contains carthamidin, iso-carthamidin, scutellarein, β-sitosterol, and stearic acid. Parts from *S. barbata,* especially parts above the ground, are typically dried for medicinal use.

Dan Shen (*Salvia miltiorrhiza*) is also known as red sage or Chinese sage. It is a perennial in the genus *Salvia* and valued for its roots in traditional Chinese medicine. One of the most abundant constituents found in *S. miltiorrhiza* is tanshinone IIA. It has been used to treat cardiovascular diseases.

Jiang Huang (*Curcuma longa,* or, Rhizome *Curcuma longa*) is the root mass (rhizoma) of turmeric, a member of the ginger family Zingiberaceae. One of its main constituents is curcumin. The dried powder of its root mass has been used to treat many cardiovascular diseases.

Tu Fu Ling (*Smilacis glabrae,* or, Rhizome *Smilacis glabrae*), the root mass (rhizoma) of *S. glabrae,* is also known as *Smilax glabra,* sarsaparilla, or *Smilacis glabrae* Rhizoma. It is used in traditional Chinese medicine for deoxidation, dampness relief and lubricating joints. Its components have been found to be anti-inflammatory and immunomodulatory, see, e.g., G. Liang et al., *Phytomedicine,*

(June, 2019) 59:152772. Its root mass, once harvested, is dried before use as medicine.

Wu Wei Zi (*Schisandra chinensis*, or, Fructus *Schisandra chinensis*) is the fruit (fructus) of *Schisandra chinensis* (northern variety) or *Schisandra sphenanthera* (southern variety), commonly known as magnolia-vine, magnolia berry, Chinese magnolia-vine, schisandra, or five-flavor-fruit (both northern and southern varieties). It is used in traditional medicine. See, e.g., Lu Y, Chen D F, "Analysis of *Schisandra chinensis* and *Schisandra sphenanthera*". *J of Chromatography A.* 1216 (11): 1980-90 (March 2009). The fruit can be dried, crushed and otherwise prepared for use.

Chai Hu (Radix *Bupleurum, Bupleurum chinense* Radix, or Radix *Bupleurum chinense*) is derived from the dried roots (radix) of *Bupleurum chinense* DC and *Bupleurum scorzonerifolium* Willd, see, Editorial Committee of Chinese Pharmacopoeia, *Chinese Pharmacopoeia*, 2015 ed. (2015, Medical Science and Technology Press, Beijing, China). It has been used for strengthening liver functions and to treat disorders such as influenza, malaria, menstrual disorders and hepatitis. See, e.g., F. Yang et al., *BioMed Research International*, 2017: 7597596 (2017).

Ling Zhi (*Ganoderma lucidum*) is considered one of the most valuable medicinal fungi or mushrooms in Chinese traditional medicine. It has been used for improving general health and to treat many disorders, often as a supplement. For example, it has been used to support cancer patients, see, e.g., J. Yuen and M. Gohel "Anticancer effects of *Ganoderma lucidum*: a review of scientific evidence," *Nutr Cancer,* 53(1):11-7 (2005). The crown of *Ganoderma lucidum* can be dried and ground into powder for mixing with other components of a formula.

Ren Shen/Ginseng (*Panax*) refers to about a dozen different varieties in the genus *Panax,* such as Korean ginseng (*P. ginseng*), South China ginseng (*P. notoginseng*), and American ginseng (*P. quinquefolius*). The root (radix) or root mass (rhizome) of ginseng can be dried after being harvested and ground into powder or sectioned into slices for medicinal use. They have been used to boost energy, lower blood sugar and cholesterol, and to revive mental acuity. The present invention's formula contemplates use of any variety of ginseng, preferably those native to Asia such as *Panax ginseng* and *Panax notoginseng.*

Bie Jia (*Carapax Trionycis,* or *Trionycis Carapax*) refers to the carapace, i.e., the dorsal section of the shell, of *Trionycis,* also known as *Trionyx sinensis Wiegmann.* The shell is dried before being ground into fine powder or otherwise processed (cooked in hot sand, for instance) into particulate forms as a medicinal ingredient. It is used for restoring yin-yang balance in recuperating patients, e.g., after a medical procedure, and for boosting immunity, see, e.g., X. Chen et al. *J Sci Food Agric.* 101(5): 2014-2026 (2021).

The extracts used in the present invention are preferably prepared for addition to the inventive compositions by, for example, grinding, crushing, comminuting, etc., a part of the herb (or animal in the case of *Trionycis*) and forming an extract by any known method including, but not limited to, dry mixing or mechanical dry blending.

The diet supplement or pharmaceutical compositions of the invention are preferably each in the form of at least one separate and distinct capsule, tablet or packet. In preferred embodiments, compositions of the invention are provided in about 1, 2, 3, 4, 5, 6, 7, or 8 grams in each distinct capsule, tablet or packet. Preferably, each form is ready for oral administration to a subject with or without the aid of drinking fluid. In an embodiment, the inventive composition needs to be dissolved in a liquid (e.g., water) before administration. Liquid containing the composition may need to be boiled, filtered before consumption.

The diet supplement or pharmaceutical compositions of the invention preferably includes a pharmaceutically acceptable carrier, additive or excipient that is suitable for oral administration. The compositions may be prepared into a solid form by any convention method known to one skilled in the art. Reference is made to, e.g., U.S. Pat. Nos. 5,911,992 and 5,985,282, the disclosure of both is incorporated by reference herein in entirety.

The expression "pharmaceutically acceptable carrier, additive or excipient" as used herein is intended to include a formulation, or substance used to stabilize, solubilize and otherwise be mixed with active ingredients to be administered to living animals, including humans. This includes any and all solvents, liquid or solid filler, diluent, excipient, encapsulating material, dispersion media, coatings, antibacterial and antifungal agents, isotonic and absorption delaying agents, and the like, compatible with pharmaceutical administration. Except insofar as any conventional media or agent is incompatible with the active compound, such use in the compositions is contemplated. Each carrier must be "acceptable" in the sense of being compatible with the other ingredients of the formulation and not injurious to a human subject. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

For a preferred embodiment of the oral administration system of the present invention, the compositions are made in the form of capsules. The preferred carrier materials for use in the capsules include stearic acid, gelatin, silica and magnesium stearate.

The present invention also provides methods of using the oral compositions of the invention to improve the health of a subject to, e.g., restore balance, boost immunity, improve metabolism, to shorten recovery time, treat a disease or disorder including cancer.

In accordance with the invention, an effective amount of the composition is administered to the patient, preferably orally. A preferred daily dosage for an adult is between about 0.3 gram and about 10 gram, more preferably, between about 1 gram and about 8 gram. The daily dosage of the oral composition preferably contains extracts from Tu Gua Gen (Radix *Trichosanthes cucumeroides*), Dan Shen (*Salvia miltiorrhiza*), Dong Chong Xia Cao (*Ophiocordyceps sinensis*), and Ling Zhi (*Ganoderma lucidum*) at a ratio of 4:2:1:1. In a more preferred embodiment, the composition further contains ten other extracts, so that the final breakdown of the composition is as follows:

1) a Tu Gua Gen (Radix *Trichosanthes cucumeroides*) extract about 20%, i.e., 18%-22%, by weight;
2) a Dan Shen (*Salvia miltiorrhiza*) extract about 10%, i.e., 9%-11%, by weight;
3) a Dong Chong Xia Cao (*Ophiocordyceps sinensis*) extract about 5%, i.e., 4.5%-5.5%, by weight;
4) a Ling Zhi (*Ganoderma lucidum*) extract about 5%, i.e., 4.5%-5.5%, by weight;
5) a Rue (*Ruta graveolens*) extract about 5%, i.e., 4.5%-5.5%, by weight;
6) a Liang Mian Zhen (*Zanthoxylum nitidum*) extract about 5%, i.e., 4.5%-5.5%, by weight;
7) a Pu Gong Ying (*Taraxacum*) extract about 5%, i.e., 4.5%-5.5%, by weight;
8) a Ban Zhi Lian (*Scutellaria barbata*) extract about 5%, i.e., 4.5%-5.5%, by weight;
9) a Jiang Huang (*Curcuma longa*) extract about 5%, i.e., 4.5%-5.5%, by weight;
10) a Tu Fu Ling (*Smilacis Glabrae*) extract about 10%, i.e., 9%-11%, by weight;
11) a Wu Wei Zi (*Schisandra chinensis*) extract about 5%, i.e., 4.5%-5.5%, by weight;
12) a Chai Hu (Radix *Bupleuri*) extract about 5%, i.e., 4.5%-5.5%, by weight;
13) a Ren Shen/Ginseng (*Panax*) extract about 5%, i.e., 4.5%-5.5%, by weight; and
14) a Bie Jia (*Carapax Trionycis*) extract about 10%, i.e., 9%-11%, by weight.

The administration of the composition is preferably daily, but not necessarily. The dosage can be divided into a plurality of sub-doses, each sub-dose being in the form of a tablet or capsule. In a preferred embodiment, the composition is administered to a patient for oral intake three times a day with four capsules/tablets each time.

TREATMENT EXAMPLES

Example 1

Male patient A, Age: 8

Patient A was diagnosed with lymphoma and leukemia when he was 4 years old. After receiving one year of chemotherapy at Beijing University Hospital, he started taking the supplement containing compositions disclosed herein for 3 years. The patient became cancer-free in 2021.

Example 2

Male patient B, Age: 55

Patient B was diagnosed with an advanced stage of nasopharyngeal carcinoma in August 2014. He received 33 treatments/regimens in radiotherapy and 12 in chemotherapy. At the beginning of 2016, he was diagnosed with advanced stage metastatic liver cancer and had surgery. He then took the supplement made according to the present invention for three consecutive years. Patient B is in good physical and mental condition in 2021.

Example 3

Male patient C, Age: 48

Patient C was diagnosed with rectal cancer in June 2017. He started taking oral supplement made according to the present invention daily. By the end of 2018, follow-up examinations indicated that he became cancer free.

Example 4

Male patient D, Age: 65

Patient D was diagnosed with esophageal thoracic cancer (4-6 thoracic vertebrae) in 2016. He started taking the supplement according to the present invention, moved to the countryside, walked and exercised every day, practiced Tai Chi, and adopted a healthier lifestyle. Two years later, Patient D was symptom free and in a better physical and mental state.

While the present invention has been particularly shown and described with reference to the structure and methods disclosed herein and as illustrated in the drawings, it is not confined to the details set forth and this invention is intended to cover any modifications and changes as may come within the scope and spirit of the following claims. All publications and patent literature described herein are incorporated by reference in entirety to the extent permitted by applicable laws and regulations.

What is claimed is:

1. A composition in the form of a tablet or a capsule, comprising a combination of extracts from each of the fourteen components as follows: Tu Gua Gen (Radix *Trichosanthes cucumeroides*), Rue (*Ruta graveolens*), Liang Mian Zhen (*Zanthoxylum nitidum*), Dong Chong Xia Cao (*Ophiocordyceps sinensis*), Pu Gong Ying (*Taraxacum*), Ban Zhi Lian (*Scutellaria barbata*), Dan Shen (*Salvia miltiorrhiza*), Jiang Huang (*Curcuma longa*), Tu Fu Ling (*Smilacis Glabrae*), Wu Wei Zi (*Schisandra chinensis*), Chai Hu (Radix *Bupleuri*), Ling Zhi (*Ganoderma lucidum*), Ren Shen/Ginseng (*Panax*), and Bie Jia (*Carapax Trionycis*).

2. The composition of claim 1 wherein extract from Tu Gua Gen (Radix *Trichosanthes cucumeroides*) is about 20% of the composition by weight.

3. The composition of claim 1 wherein extract from Rue (*Ruta graveolens*) is about 5% of the composition by weight.

4. The composition of claim 1 wherein extract from Liang Mian Zhen (*Zanthoxylum nitidum*) is about 5% of the composition by weight.

5. The composition of claim 1 wherein extract from Dong Chong Xia Cao (*Ophiocordyceps sinensis*) is about 5% of the composition by weight.

6. The composition of claim 1 wherein extract from Pu Gong Ying (*Taraxacum*) is about 5% of the composition by weight.

7. The composition of claim 1 wherein extract from Ban Zhi Lian (*Scutellaria barbata*) is about 5% of the composition by weight.

8. The composition of claim 1 wherein extract from Dan Shen (*Salvia miltiorrhiza*) is about 10% of the composition by weight.

9. The composition of claim 1 wherein extract from Jiang Huang (Curcuma longa) is about 5% of the composition by weight.

10. The composition of claim 1 wherein extract from Tu Fu Ling (*Smilacis Glabrae*) is about 10% of the composition by weight.

11. The composition of claim 1 wherein extract from Wu Wei Zi (*Schisandra chinensis*) is about 5% of the composition by weight.

12. The composition of claim 1 wherein extract from Chai Hu (Radix *Bupleuri*) is about 5% of the composition by weight.

13. The composition of claim 1 wherein extract from Ling Zhi (*Ganoderma lucidum*) is about 5% of the composition by weight.

14. The composition of claim 1 wherein extract from Ren Shen/Ginseng (*Panax*) is about 5% of the composition by weight.

15. The composition of claim 1 wherein extract from Bie Jia (*Carapax Trionycis*) is about 10% of the composition by weight.

16. A composition in the form of a tablet or a capsule, comprising:

(1) a Tu Gua Gen (Radix *Trichosanthes cucumeroides*) extract about 20% by weight;

(2) a Rue (*Ruta graveolens*) extract about 5% by weight;

(3) a Liang Mian Zhen (*Zanthoxylum nitidum*) extract about 5% by weight;

(4) a Dong Chong Xia Cao (*Ophiocordyceps sinensis*) extract about 5% by weight;

(5) a Pu Gong Ying (*Taraxacum*) extract about 5% by weight;

(6) a Ban Zhi Lian (*Scutellaria barbata*) extract about 5% by weight;

(7) a Dan Shen (*Salvia miltiorrhiza*) extract about 10% by weight;

(8) a Jiang Huang (*Curcuma longa*) extract about 5% by weight;

(9) a Tu Fu Ling (*Smilacis Glabrae*) extract about 10% by weight;

(10) a Wu Wei Zi (*Schisandra chinensis*) extract about 5% by weight;

(11) a Chai Hu (Radix *Bupleuri*) extract about 5% by weight;

(12) a Ling Zhi (*Ganoderma lucidum*) extract about 5% by weight;

(13) a Ren Shen/Ginseng (*Panax*) extract about 5% by weight; and

(14) a Bie Jia (*Carapax Trionycis*) extract about 10% by weight.

17. The composition of claim 1 as a supplement to a person's diet.

18. The composition of claim 1 as a pharmaceutical.

19. The composition of claim 18, further comprising a pharmaceutically acceptable carrier, additive or excipient.

\* \* \* \* \*